(12) United States Patent
Gajjar et al.

(10) Patent No.: US 11,428,641 B2
(45) Date of Patent: Aug. 30, 2022

(54) GEMSTONE VERIFICATION

(71) Applicant: Sahajanand Technologies Private Limited, Gujarat (IN)

(72) Inventors: Munjal Dhirajlal Gajjar, Gujarat (IN); Chetan Fulchandbhai Patel, Nagalpur (IN); Piyush Himmatbhai Vaishnani, Bardoli (IN); Rahul Mahendrakumar Gaywala, Gujarat (IN)

(73) Assignee: Sahajanand Technologies Private Limited, Gujarat Surat (IN)

( * ) Notice: Subject to any disclaimer, the term of this patent is extended or adjusted under 35 U.S.C. 154(b) by 202 days.

(21) Appl. No.: 15/733,159

(22) PCT Filed: Dec. 24, 2018

(86) PCT No.: PCT/IB2018/060586
§ 371 (c)(1),
(2) Date: May 31, 2020

(87) PCT Pub. No.: WO2019/123439
PCT Pub. Date: Jun. 27, 2019

(65) Prior Publication Data
US 2020/0355618 A1    Nov. 12, 2020

(30) Foreign Application Priority Data
Dec. 22, 2017  (IN) .............................. 201721046430

(51) Int. Cl.
*G01N 21/87*    (2006.01)
*B28D 5/04*     (2006.01)
*G01N 33/38*    (2006.01)

(52) U.S. Cl.
CPC .............. *G01N 21/87* (2013.01); *B28D 5/04* (2013.01); *G01N 33/381* (2013.01)

(58) Field of Classification Search
CPC .......... G01N 33/381; G01N 21/87; B28D 5/04
See application file for complete search history.

(56) References Cited

U.S. PATENT DOCUMENTS

2006/0196858 A1    9/2006    Barron et al.
2007/0186918 A1    8/2007    Ceulemans

FOREIGN PATENT DOCUMENTS

| CN | 106217666 A | * | 12/2016 |
| IN | 26/2017 | | 6/2017 |

(Continued)

OTHER PUBLICATIONS

"International Application No. PCT/IB2018/060586, International Search Report and Written Opinion dated Mar. 18, 2019", (dated Mar. 18, 2019), 13 pgs.

*Primary Examiner* — Maurice C Smith
(74) *Attorney, Agent, or Firm* — Schwegman Lundberg & Woessner, P.A.

(57) ABSTRACT

Examples of gemstone verification are described herein. In one example, for processing a gemstone, pre-stored marking coordinates associated with a gemstone ID are obtained, the pre-stored marking coordinates generated during planning phase of the processing. Further, real-time marking coordinates for the gemstone to be processed are also obtained. An identity of the gemstone is verified based on a comparison of the pre-stored marking coordinates with the real-time marking coordinates. Further, information, including cutting parameters, associated with the gemstone ID of the gemstone is retrieved in response to a valid verification of the identity of the gemstone, for processing the gemstone.

10 Claims, 15 Drawing Sheets

(56) References Cited

FOREIGN PATENT DOCUMENTS

| | | | | |
|---|---|---|---|---|
| JP | 2004034259 A | * | 2/2004 | |
| WO | WO-2006117406 A2 | * | 11/2006 | ............. G01N 21/87 |
| WO | WO-2012001698 A1 | * | 1/2012 | ........... B23K 26/032 |
| WO | WO-2012001698 A1 | | 1/2012 | |
| WO | WO-2016092568 A2 | | 6/2016 | |
| WO | WO-2019123439 A1 | | 6/2019 | |

* cited by examiner

GEMSTONE VERIFICATION

PRIORITY CLAIM TO RELATED APPLICATIONS

This application is a U.S. national stage filing under 35 U.S.C. § 371 from International Application No. PCT/IB2018/060586, filed on 24 Dec. 2018, and published as WO2019/123439 on 27 Jun. 2019, which claims the benefit under 35 U.S.C. 119 to India Application No. 201721046430, filed on 22 Dec. 2017, the benefit of priority of each of which is claimed herein, and which applications and publication are hereby incorporated herein by reference in their entirety.

TECHNICAL FIELD

The present subject matter relates, in general, to gemstone technology and, particularly but not exclusively, to gemstone processing.

BACKGROUND

Gemstones are naturally occurring deposits of minerals and can include, for example, diamonds, quartz, opals, sapphires, rubies, emeralds, and topaz. Since the gemstones are rare, they are highly valued for use, say in ornamentation and jewellery. The value of these gemstones results from their color, luster, and the manner in which they transmit, refract, or reflect rays of light. For the enhancement of such properties, rough gemstones are processed, for instance, by cutting, faceting, shaping, and polishing. The processing of the gemstone imparts certain characteristics to a gemstone. For example, the value of a processed gemstone is generally determined by the 4Cs, i.e., carat (weight), clarity (transparency), color, and cut which are directly or indirectly affected by the processing technique. Therefore, techniques for effective gemstone processing have been areas of active research.

BRIEF DESCRIPTION OF DRAWINGS

The detailed description is described with reference to the accompanying figures. In the figures, the left-most digit(s) of a reference number identifies the figure in which the reference number first appears. The same numbers are used throughout the drawings to reference like features and components.

DETAILED DESCRIPTION

Figure 1:
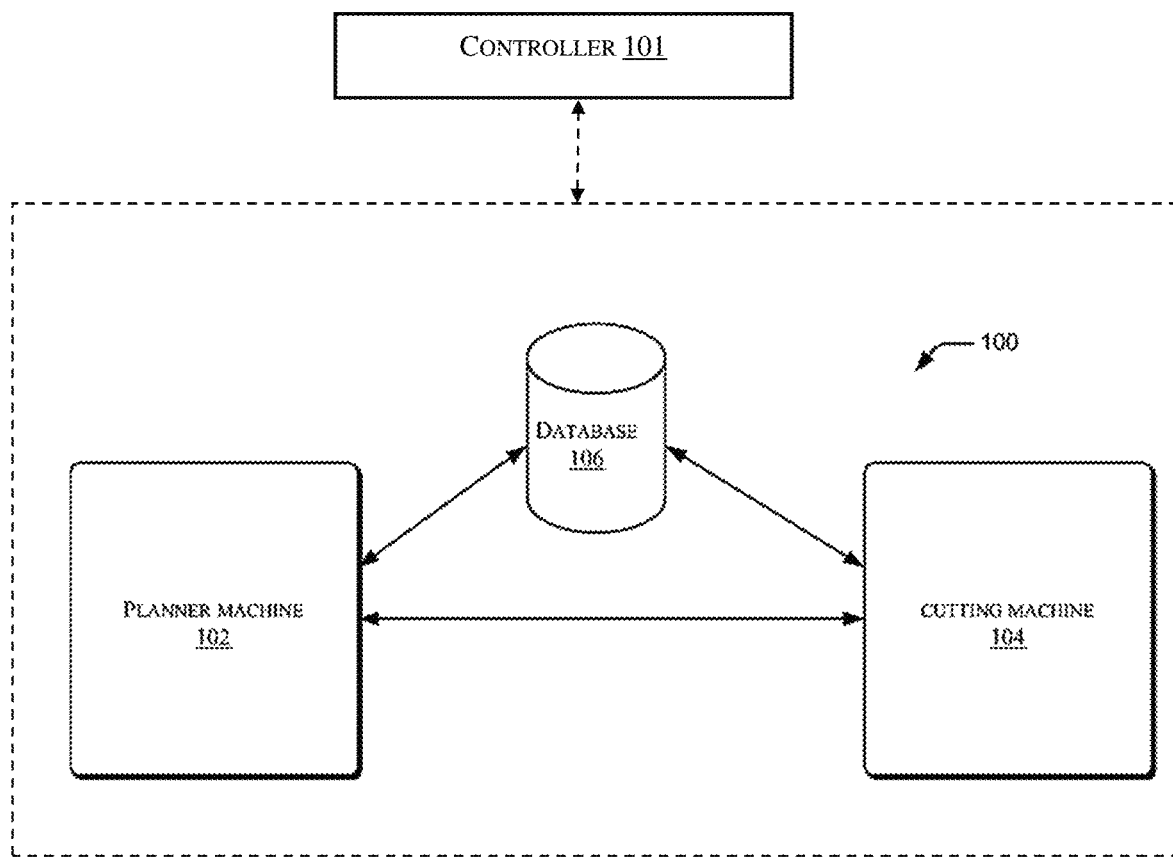
FIG. 1 illustrates a schematic of a gemstone processing system for processing and verifying gemstones, in accordance with an example of the present subject matter.

The present subject matter relates to aspects relating to processing of gemstones. As mentioned previously, in recent times techniques which facilitate effective processing of gemstones have been areas of active research. As part of gemstone processing, the gemstone is assessed for planning the cutting and polishing in order to obtain the best value gemstone, for example, in terms of size. Once the planning is done, the gemstone is marked on its surface to indicate the references for further processing the gemstone. The markings can include table cutting marking, girdle bruiting marking, etc. Conventionally, the planning is done manually and, on the basis of the planning, a laser is used for marking the gemstone. Subsequently, when the gemstone is to be processed further, the gemstone is mounted in a holder or a spindle in a laser cutting machine, and manually oriented based on the markings. Once mounted and oriented, the gemstone is processed further.

However, since the steps involved in gemstone processing are manual-skill-intensive, the entire process is low on productivity. In addition, the steps involve a substantial degree of skill on the manual labour, any absence leads to low quality of processing of the gemstone. For example, the table line and its relative marking line detection is done manually by setting and rotating the gemstone at various degrees to fetch the starting point of cutting the table portion of the gemstone for initiating the cutting process. Such manual setting increases the setting time and hence the number of gemstones processed in a given period of time is substantially low. Also, this setting of gemstone requires a high level of expertise and any lack of it may lead to a loss in value of the processed gemstone. In addition, there is low consistency in centering and adjustment of the gemstone, since the assessment is subjective and varies from person to person. Further, the gemstone is manually adjusted to set it at its required position by using a small hammer on a gemstone die in the spindle of the cutting machine. This hammering requires a high degree of skill and may ultimately affect the rotary spindle life.

Further, the verification of the correct center detection is not done due to which, the gemstone is not cut exactly as per the requirement which ultimately affects the production. In addition, there is no verification as to whether the gemstone that is being mounted and processed is the same as the one for which the planning information is being used for mounting and processing.

To address the abovementioned problems, the techniques according to the present subject matter provide for automatic verification of the rough gemstone at the time of commencement of the gemstone processing operation, for example, before the cutting operation. In one example, for verifying and processing a gemstone, for example, for cutting, pre-stored marking coordinates associated with a gemstone ID are obtained, the pre-stored marking coordinates generated during planning phase of the processing. Further, real-time marking coordinates for the gemstone to be processed are also obtained. An identity of the gemstone is verified based on a comparison of the pre-stored marking coordinates with the real-time marking coordinates. Further, information, including cutting parameters, associated with the gemstone ID of the gemstone is retrieved in response to a valid verification of the identity of the gemstone, for processing the gemstone.

The present subject matter relates to a system and a method for gemstone verification and processing, and also includes within its purview a non-transitory computer readable media having instructions recorded thereon for gemstone verification and processing.

These and other advantages of the present subject matter would be described in greater detail in conjunction with the following figures. While aspects of gemstone verification and processing can be implemented in any number of different configurations, the embodiments are described in the context of the following device(s) and method(s).

FIG. 1 illustrate schematics of a gemstone processing system 100 for processing and verifying a gemstone, such as a rough gemstone, in accordance with an embodiment of the present subject matter. The gemstone processing system 100, among other things, includes a controller 101 for the gemstone processing system 100, in accordance with an embodiment of the present subject matter. In said embodiment, the controller 101 can be implemented as a micro-controller, a microcomputer, and/or any device that manipulates signals based on operational instructions.

According to said embodiment, the controller 101 can include a processor and a device memory. The processor can be a single processing unit or a number of units, all of which could include multiple computing units. The processor may be implemented as one or more microprocessors, microcomputers, microcontrollers, digital signal processors, central processing units, state machines, logic circuitries, and/or any devices that manipulate signals, based on operational instructions. Among other capabilities, the processor(s) is provided to fetch and execute computer-readable instructions stored in the device memory. The device memory may be coupled to the processor and can include any computer-readable medium known in the art including, for example, volatile memory, such as static random-access memory (SRAM) and dynamic random-access memory (DRAM), and/or non-volatile memory, such as read only memory (ROM), erasable programmable rom, flash memories, hard disks, optical disks, and magnetic tapes.

Further, the controller 101 may include module(s) and data. The modules and the data may be coupled to the processor. The modules, amongst other things, include routines, programs, objects, components, data structures, etc., which perform particular tasks or implement particular abstract data types. The modules may also, be implemented as, signal processor(s), state machine(s), logic circuitries, and/or any other device or component that manipulate signals based on operational instructions. In addition, the modules may include programs or coded instructions that supplement applications or functions performed by the controller 101.

Additionally, in said implementation, the data amongst other things, may serve as a repository for storing data that is processed, received, or generated, as a result of the execution of one or more modules in the module(s). Although the data is shown internal to the controller 101, it may be understood that the data can reside in an external repository (not shown in the figure), which may be operably coupled to the controller 101. Accordingly, the controller 101 may be provided with input/output (i/o) interface(s) (not shown) to communicate with the external repository to obtain information from the data. The i/o interfaces may include a variety of software and hardware interfaces, which may enable the controller 101 to communicate with the external repository and peripheral components of the gemstone processing system 100.

The controller 101, when deployed in the gemstone processing system 100, performs the functions of the gemstone processing system 100. For the sake of brevity and ease of understanding, the description, henceforth, is explained with reference to the gemstone processing system 100 and the operation and functions performed by it, it will be understood that the functions and operations are interchangeably performed by the controller 101 of the gemstone processing system 100, wherever and as appropriately understood by a person skilled in the art. For example, the processor 101 can be a part of the cutting machine 104 for performing the operation of the cutting machine 104 as well as be a part of the planning machine 102 to perform the functions of the planning machine 102. As will be understood, the planning machine 102 and the cutting machine 104 may have separate processors 101 for their individual operation, or may share a common processor 101.

The gemstone processing system 100 further includes a planning machine 102 and a cutting machine 104. As part of gemstone processing system 100, the planning machine 102 scans the rough gemstone to measure basic geometry thereof. Thereafter, the planning machine 102 estimates physical attributes of the gemstone, for instance, based upon the geometry of the gemstone, and stores it for further use. In addition to the markings, a rough gemstone ID can be generated and associated with the gemstone for which the marking has been done.

Further, at the planning machine 102 itself, based on the estimated attributes, the gemstone undergoes a marking process. The planning machine 102 includes a marking laser where the marking laser forms various marking patterns on the surface of the gemstone. These marking patterns may be considered to be the reference marks of various portions of gemstone for further cutting process of that rough gemstone.

The physical attributes, the associated rough gemstone ID, and other information generated may be transferred further to the cutting machine 104 for further cutting process. For example, the information, in addition, can include the image of the markings, for instance, the marking line and the table line. This image can be used later for matching and verifying the gemstone and for correctly orienting the gemstone for cutting, as will be explained later. In one example, the information regarding the rough gemstone, as mentioned above, generated in the planning machine 102 can be stored in the database 106, which can be accessed by the cutting machine 104 to retrieve such information.

Further, from the planning machine 102, the gemstone may be sent to the cutting machine 104 which includes a laser cutting machine for cutting the gemstone as planned in the planning machine 102. For the same, the rough gemstone ID, created in the planning machine 102, is entered and the information relating to the gemstone, as mentioned above, is extracted from the database 106 in which the information was saved after obtaining from the planning machine 102. In another example, the cutting machine 104 can obtain the information for that gemstone ID from the planning machine 102 on the fly, i.e., as and when the gemstone is to be processed, the cutting machine 104 may query the planning machine 102 regarding the gemstone ID of the rough gemstone and obtain the information. As mentioned previously, the data may be the physical attributes of the gemstone, its various 3D markings, say table cutting marking, girdle bruiting marking, etc. marking coordinates indicating the actual markings on the gemstone. For instance, the cutting machine 104 obtains the data of all the coordinates of each marking and other physical attributes to generate an image, such as a 3D image, of the rough gemstone to be processed further.

Once all the information relating to the gemstone which is set for process, is extracted; the gemstone is mounted in a holder in a rotation table and the center detection of the gemstone takes place for proper alignment of the gemstone. The alignment mechanism of the gemstone processing system, in an automated manner, accurately and efficiently aligns the gemstone placed on the holder in the rotation table before the initialization of the gemstone cutting. In an example, the center detection of the gemstone is performed in the manner as described in the Indian Patent Application no. 201621016861, previously filed in the name of the present Applicant and incorporated herein by reference.

Further, the cutting machine 104 includes an image capturing device to capture real-time image data for a desired surface of the gemstone. For example, the top surface or the table view of the gemstone, is captured by means of the scanning device or the image capturing device. The captured image is then analyzed by the gemstone processing system 100 to determine whether the marking lines on the captured image are matching with the marking coordinates (or the image) of the gemstone that was obtained from the planning machine 102. In other terms, the real-time image of the gemstone with the actual markings is superimposed with the image of the markings previously stored to determine whether the markings match beyond a predetermined threshold. If the match is beyond the threshold, say 90% or 95%, then the gemstone mounted in the cutting machine 104 at that moment is identified and verified to be the same gemstone for which the data has been obtained and the cutting parameters are also obtained.

In another case, the maximum extent of match between the markings on the real-time image and the marking coordinates on the image from the planning machine 102 is considered to be the best-match. This means that all the images/marking coordinates obtained from the planning machine 102 or the database 106 are compared, one by one, with the real-time image/coordinates, and the images/marking coordinates that match the real-time image/coordinates to the maximum extent are selected as the best-match.

For matching the two images, the marking coordinates extracted from the planning machine 102 are rotated through 360 degrees while superimposed over the real-time captured image of the gemstone. At each predetermined interval of rotation, say 1 degree or 0.5 degree of rotation, the two images are matched to determine the percentage of match. Once the 360 degrees rotation of one image relative to the other is completed, the best-match, i.e., the images having the highest percentage of matching is assessed as to whether it is above the predetermined threshold match or not. For example, when rotated by 1 degree rotation, the marking coordinates or the image from the planning machine 102 is rotated 360 times. The no. of times the image matches against the total number of times it is matches, i.e., 360 times, provides the percentage match. In another example, the extent of match or the number of the coordinates that match per rotation or in the total number of rotations, as the case may be, can be used for determining the percentage match. Other modes of determining the percentage match, as envisaged by a person skilled in the art, are also considered to be a part of the present subject matter.

If the match is greater than the threshold, then the gemstone is verified as identified and is further processed. If the match is less than the threshold percentage, then the gemstone is rejected for further processing as being mismatched or unverified. Operator intervention may be required by the system 100 in such a case.

Figure 2A:
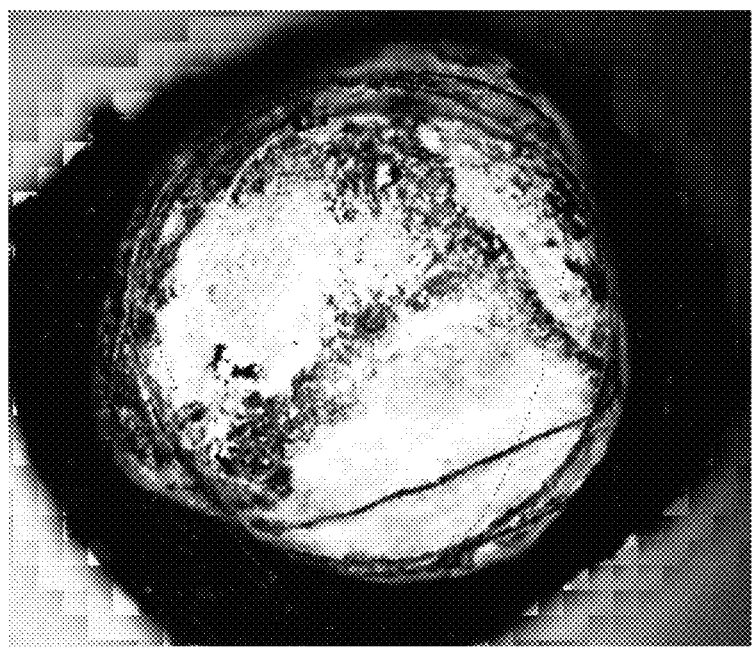
FIG. 2A to 2E illustrate captured images of a gemstone from a table view direction superimposed with marking coordinates at various degrees of relative rotation between the captured images and the marking coordinates for matching for gemstone verification and processing, in accordance with an example of the present subject matter.
Figure 2B:
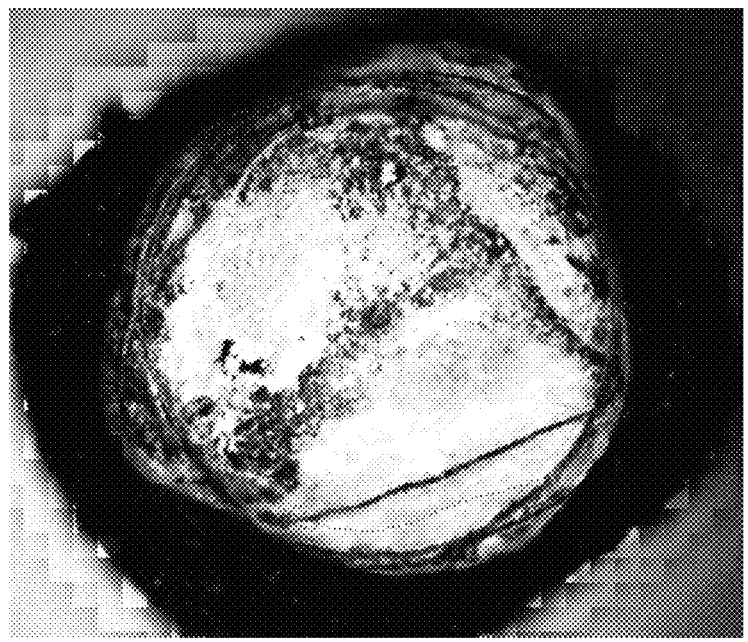
Figure 2C:
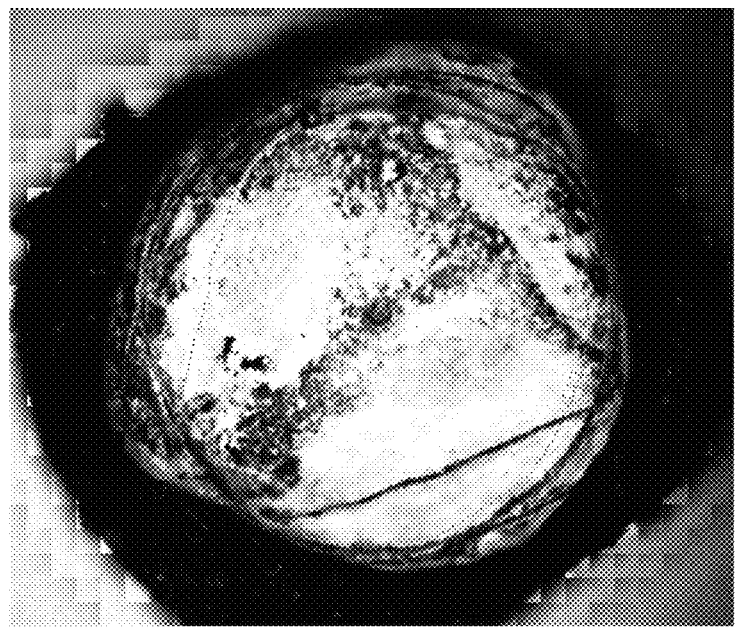
Figure 2D:
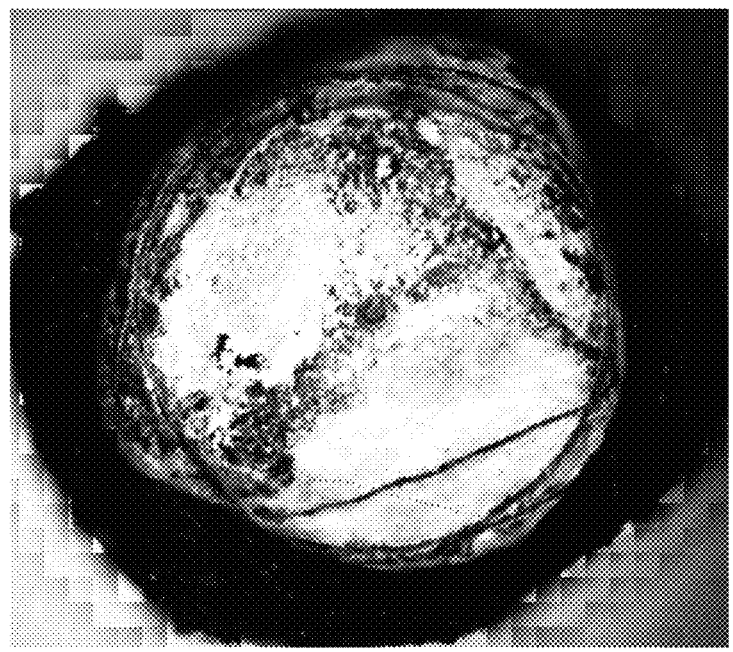
Figure 2E:
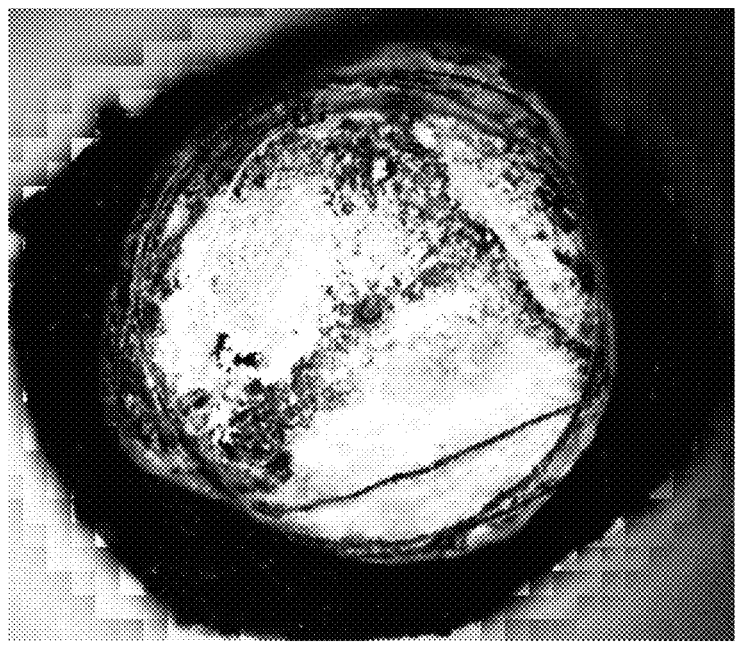

FIG. 2A to show various images captured by the image capturing device from the table view or the top view of the gemstone and superimposed with the image of the marking coordinates at various degrees. For example, FIG. 2A shows the two superimposed images at 0 degree of rotation, FIG. 2B illustrates the two superimposed images at 90 degrees of rotation, FIG. 2C shows the two superimposed images at 180 degrees of rotation, and FIG. 2D shows the two superimposed images at 270 degrees of rotation. FIG. 2E shows the two superimposed images at 323 degrees at which the best-match takes place between the two images. The blue and red dots shown are the marking coordinates extracted from the planning machine 102. The black line markings done are the actual markings on the gemstone created by the laser in the planning machine 102 which are matched with the marking coordinates, i.e., the blue and red dots.

In one example of the present subject matter, the system 100 may not only provide for quick verification of the gemstone but also provide for a manner of achieving automated orientation of the diamond in a predetermined position in which the best cutting efficiency, and therefore, high productivity of gemstone processing can be achieved.

Accordingly, in the planning stage, i.e., the planning machine 102 considers or also annotates a reference for finding a table line of the gemstone. The table line is the marking from which the cutting operation commences for highest efficiency and productivity. For example, the planning machine 102 determines the degree of rotation that is to be made with respect to the marking coordinates and passes the information to the cutting machine 104. In another example, in addition to the degree of rotation, the direction of rotation can also be passed from the planning machine to the cutting machine 104. and the direction in which the rotation is to be effected to obtain the alignment with the table line. This is the aspect related to table line detection of the gemstone. For an example, the 30 degrees (obtained from the planning machine 102 along with the other marking coordinates) from the reference point (323 degrees) is the table line. Then, the final degree at which the table line is obtained will be 323+30=353 degrees. Therefore, once the table line is automatically detected and the gemstone is oriented correctly, the cutting starts at the table line.

Figure 3A:
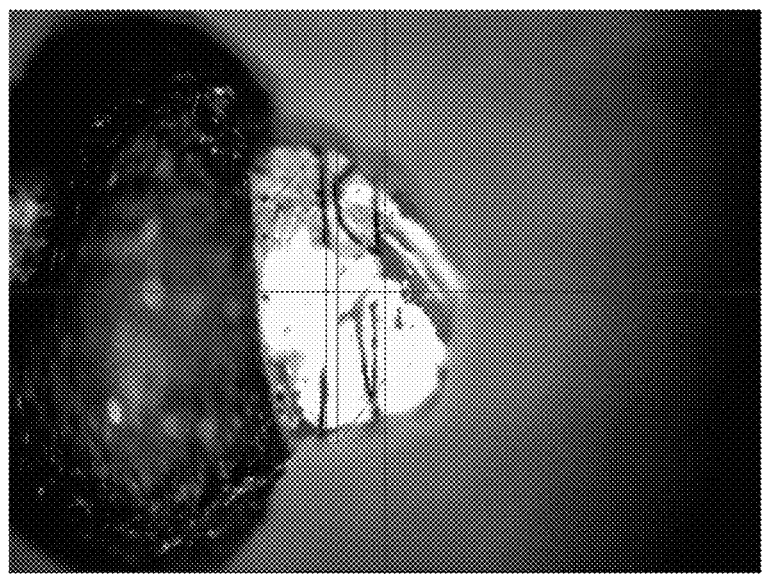
FIGS. 3A to 3H illustrate captured images of the gemstone superimposed with the marking coordinates in a table cutting view at various degrees of relative rotation between the marking coordinates and the captured images, in accordance with an example of the present subject matter.
Figure 3B:
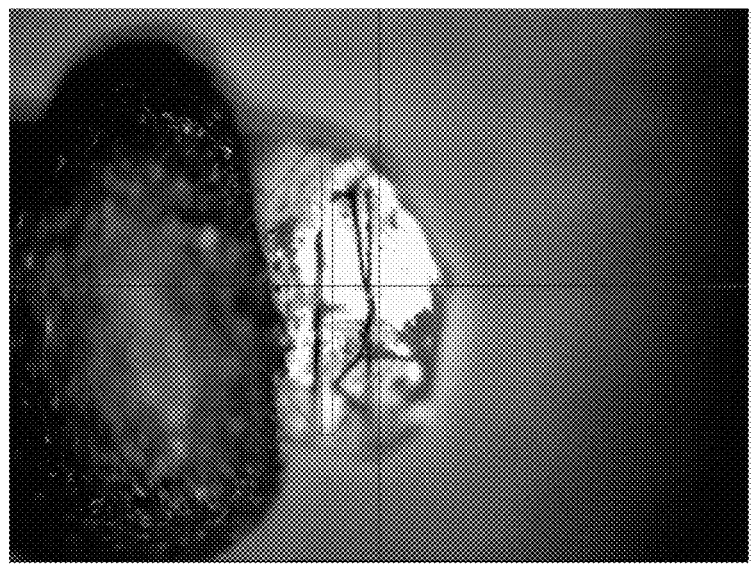
Figure 3C:
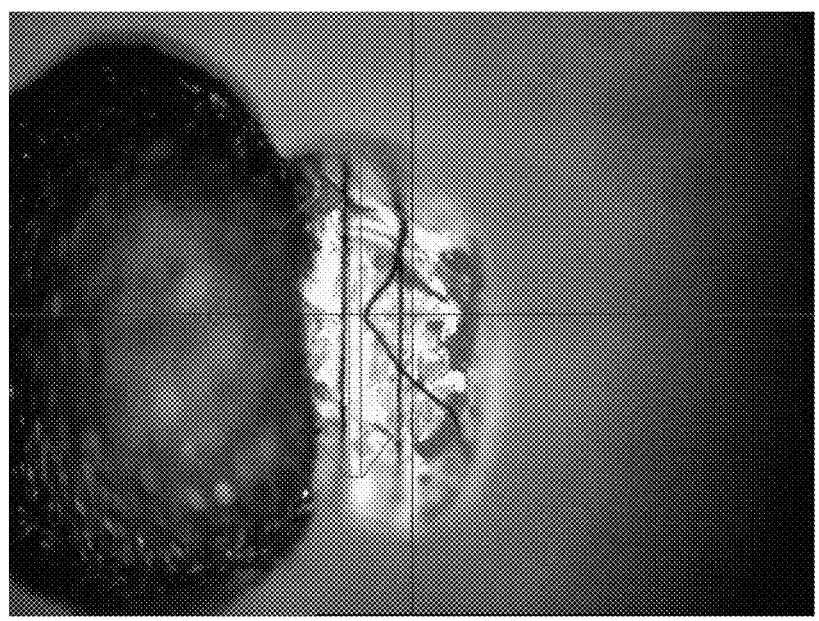
Figure 3D:
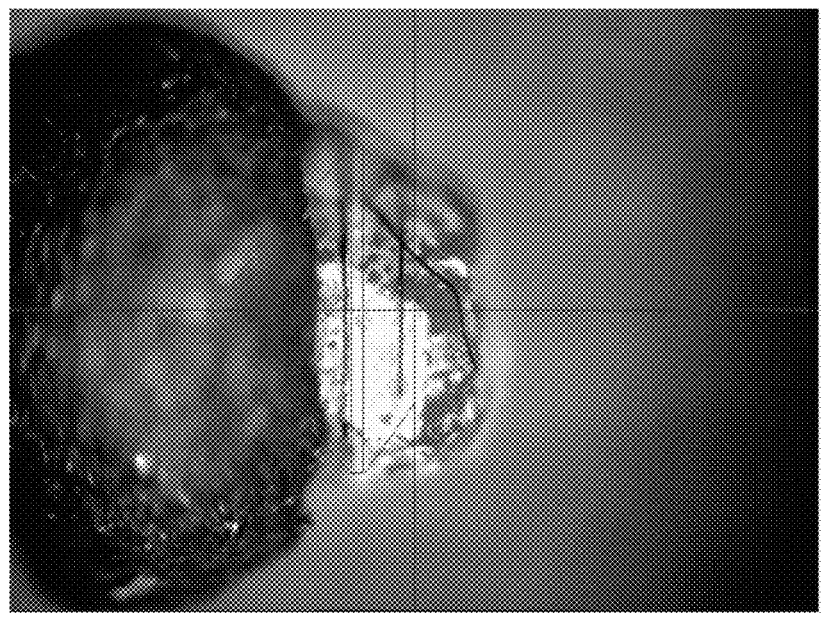
Figure 3E:
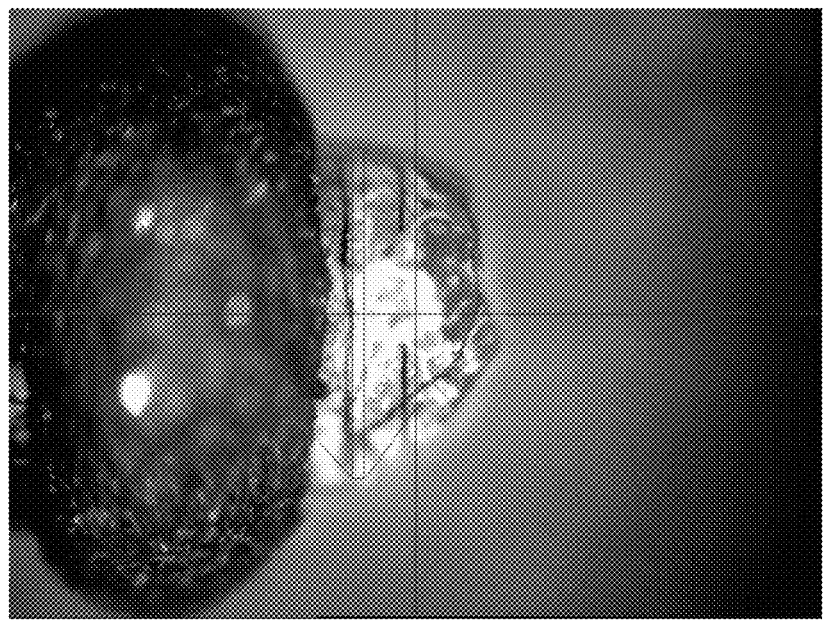
Figure 3F:
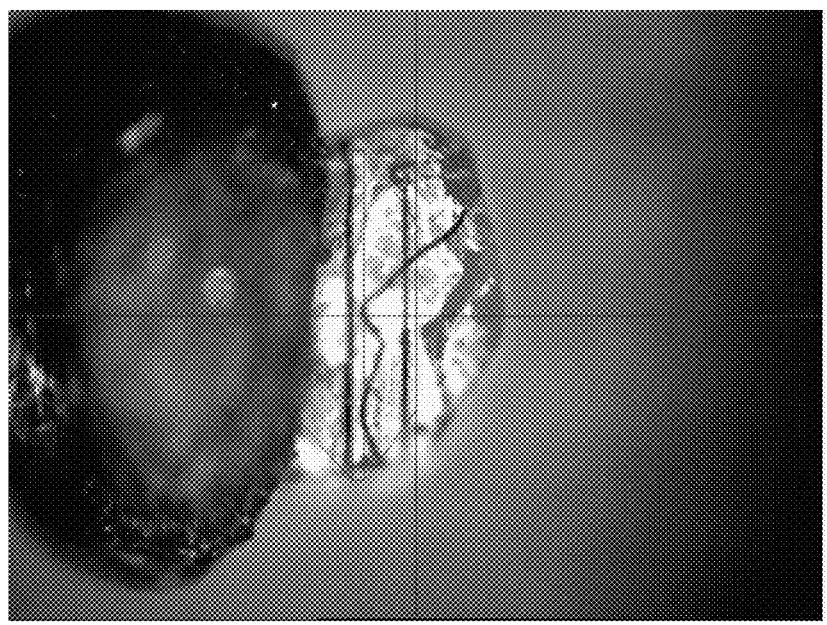
Figure 3G:
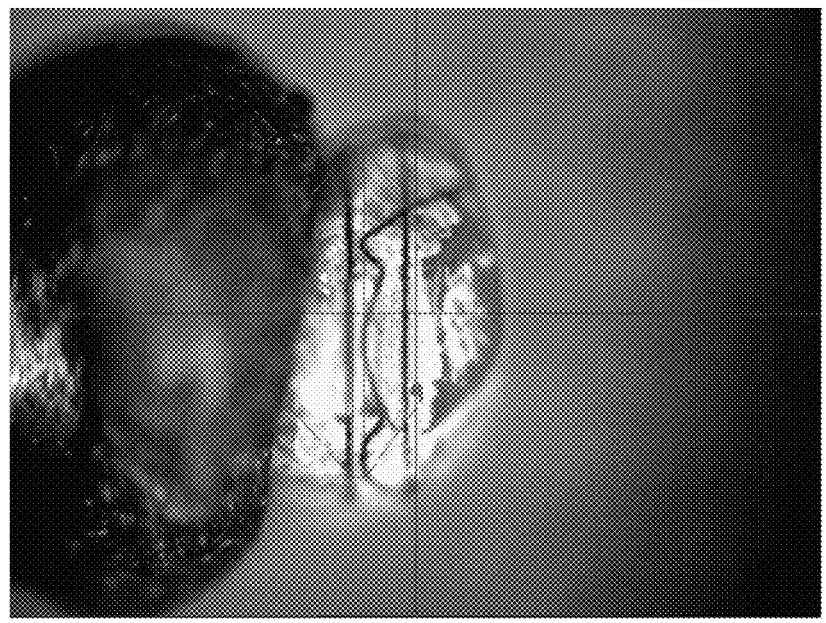
Figure 3H:
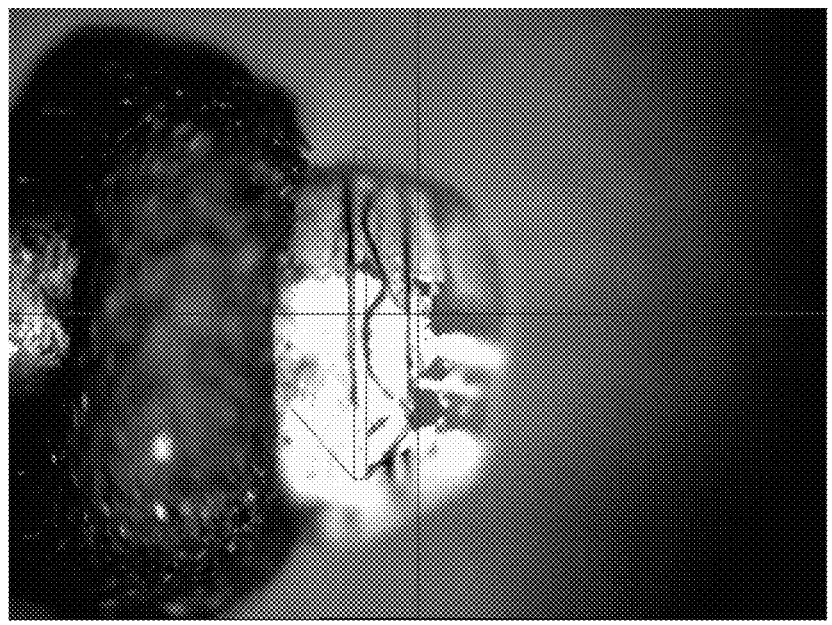

The table line detection achieved by the cutting machine 104 of the system 100 is illustrated in FIGS. 3A to 3H. FIGS. 3A to 3H illustrate captured images of the gemstone superimposed with the marking coordinates in a table cutting view at various degrees of relative rotation between the marking coordinates and the captured images. For example, FIG. 3A shows the two superimposed images at 0 degree of rotation, FIG. 3B illustrates the two superimposed images at 45 degrees of rotation, FIG. 3C illustrates the two superimposed images at 90 degrees of rotation, FIG. 3D illustrates the two superimposed images at 135 degrees of rotation, FIG. 3E shows the two superimposed images at 180 degrees of rotation, FIG. 3F illustrates the two superimposed images at 225 degrees of rotation, FIG. 3G shows the two superimposed images at 270 degrees of rotation, and FIG. 3H illustrates the two superimposed images at 315 degrees of rotation. FIG. 3G shows the two superimposed images at the position in which the best-match takes place between the two images.

In FIG. 3G, the best-match obtained is at 270 degrees. FIG. 3G shows that at 270 degrees, the flat surface of the gemstone, i.e., the table is as required and the cutting depth is at minimum which makes it the most appropriate orientation for cutting the gemstone properly and rapidly. As explained above, this entire process is automated and does not involve operator-intervention at all affording a high efficiency, productivity, and accuracy to the process. Again, in FIGS. 3A to 3H, the blue and red dots shown are the marking coordinates extracted from the planning machine 102. The black line markings done are the actual markings, referred to as the table line markings, on the gemstone by the laser in the planning machine 102 which are matched with the marking coordinates, i.e., the blue and red dots.

The present subject matter, therefore, provides for high production rate, automation of cross-verification of gemstone, verification of gemstone correctness (i.e., whether the correct gemstone is received for cutting), and automatic table line detection which ultimately reduces the stone setting time and further increases productivity.

Figure 4:
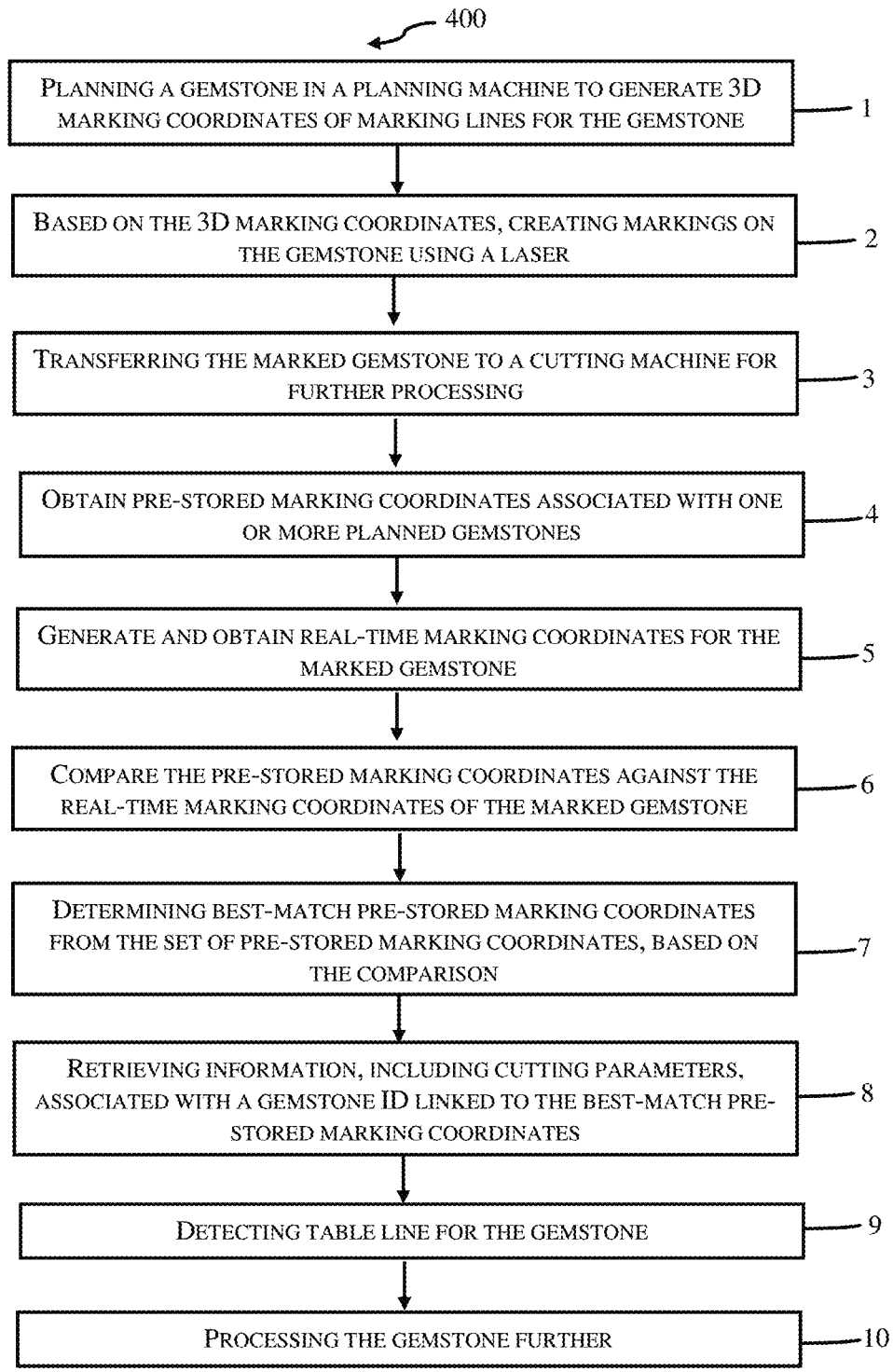
FIG. 4 illustrates a method for verifying and processing a gemstone, according to an example of the present subject matter

FIG. 4 illustrates a method 400 for verifying and processing a gemstone, according to an implementation of the present subject matter. The order in which the method steps are described below is not intended to be construed as a limitation, and any number of the described method steps can be combined in any appropriate order to execute the method or an alternative method. Additionally, individual steps may be deleted from the method without departing from the spirit and scope of the subject matter described herein.

The method 400 can be performed by programmed computing devices, for example, based on instructions retrieved from non-transitory computer readable media. The computer readable media can include machine-executable or computer-executable instructions to perform all or portions of the described method. The computer readable media may be, for example, digital memories, magnetic storage media, such as a magnetic disks and magnetic tapes, hard drives, or optically readable data storage media.

In the present example, the method 400 may be performed by the gemstone processing system 100 and the controller 101 of the gemstone processing system 100. For the sake of brevity of description, the components of the gemstone processing system 100 performing the various steps of the method are not described in detail below. Such details are provided in the description with reference to the above figures.

At block 1, a gemstone is planned in the planning machine 102 where the basic geometry of the gemstone is scanned. The physical attributes of the gemstone based upon the geometry of the gemstone and all the 3D marking coordinates of all the marking lines will be generated along with the 3D profile of the gemstone.

At block 2, based on the 3D marking coordinates, the markings on the gemstone will be made by the laser in the planning machine 102 itself. All the data from block 1 and block 2 is stored for further use. For example, the marking coordinates along with all the physical attributes are stored in the database 106.

At block 3, the marked gemstone is transferred to the cutting machine 104 for further cutting process.

At block 4, in the cutting machine 104, the rough gemstone ID is entered. Upon doing so, the cutting machine 104 obtains the data of all the coordinates of each marking and other physical attributes of the gemstone ID from planning machine 102 database 106. In another case, the data can be obtained from the planning machine 102 after the completion of the marking of the gemstone and stored in the database of the cutting machine 104. In another example, irrespective of the gemstone ID, all the pre-stored marking coordinates associated with all the planned gemstones in the planning machine 102 are obtained by the cutting machine 104. In other words, the entire set of pre-stored marking coordinates created during the planning stage can be retrieved by the cutting machine 104, either from the planning machine 102 or the database 106.

At block 5, real-time marking coordinates are generated for the marked gemstone. For instance, the image data for the desired surface (for example, table view or top view) of the marked gemstone is captured by means of a scanning device or an image capturing device.

At block 6, the pre-stored marking coordinates are compared with respect to the real-time marking coordinates of the marked gemstone. For example, the pre-stored marking coordinates from the information obtained from the database or the planning machine 102, can be superimposed with respect to the real-time marking coordinates of the marked gemstone in a coordinate space, for example, in a 3-dimensional (3D) coordinate space. In another example, the captured image is analyzed to match the real-time marking coordinates on the captured image with the marking coordinates obtained from the planning machine 102. In said example, image of the gemstone indicating the real-time marking coordinates is superimposed with the image of the marking coordinates previously stored and matched.

In one case, the images indicating the pre-stored marking coordinates, extracted from the planning machine 102 or the database 106, are relatively rotated with respect to the captured image indicating the real-time-determined marking coordinates for the marked gemstone, around 360 degrees with reference to the Z-axis of the marked gemstone and compared for matching at predetermined intervals of rotation. For example, at each predetermined interval of rotation, say 1 degree or 0.5 degree of rotation, the two images, i.e., the coordinates and the captured image, are matched to determine a percentage of match.

At block 7, once the comparison of the two marking coordinates is completed, the best-match is determined. In an example, all the matched pre-stored marking coordinates have a percentage of match associated therewith, and they are all assessed as to whether any is above the predetermined threshold match or not. If the match is greater than the threshold, then the gemstone is verified and is further processed. If the match is less than the threshold percentage, then the gemstone is rejected for further processing as being mismatched or unverified.

At block 8, the information, including cutting parameters, associated with a gemstone ID linked to the best-match pre-stored marking coordinates is retrieved. This is achieved in response to the valid verification of the identity of the gemstone at block 8 and the information so retrieved is used for processing the marked gemstone At block 9, once the best-match is achieved, the table line detection of the gemstone takes place, based on a relative position between the two images at which the best-match is obtained. For example, the table line for the gemstone is detected based on a best-match position of the image indicative of the real-time marking coordinates relative to the image indicative of the pre-stored marking coordinates. The degree of relative rotation between the two images, at which the best-match is obtained, is considered to be the reference for finding the table line. This information is obtained from the planning machine 102 database 106 as part of the information obtained in block 5. For an example, if the table line is at 30 degrees rotation in the clockwise direction (obtained from the planning machine 102 along with the other marking coordinates) from the reference point (i.e., the marking line, say aligned at 323 degrees of rotation), then, the final degrees of rotation at which the table line is obtained will be 323+30=353 degrees.

At block 10, once the table line is automatically detected, the cutting machine 104 processes the gemstone further for cutting at the table line. For example, the gemstone can be rotated at 90 degrees about the U-axis and the table line cutting starts.

The present subject matter also envisages a non-transitory computer readable medium for processing and verifying gemstones, according to an example of the present subject matter. The non-transitory computer readable medium can be, for example, an internal memory device or an external memory device. The non-transitory computer readable medium may also be communicatively coupled to data sources over a network. The data sources can include, for example, database 106s and computing devices. In one example, the non-transitory computer readable medium includes a set of computer readable instructions, such as the modules of the controller 101 of the gemstone processing system 100. The set of computer readable instructions, referred to as instructions hereinafter, can be accessed by a processing resource and subsequently executed to perform acts for gemstone verification and processing.

Although implementations for gemstone verification and processing are described, it is to be understood that the present subject matter is not necessarily limited to the specific features of the systems or methods or other aspects described herein. Rather, the specific features are disclosed as implementations for gemstone verification and processing.

We claim:

1. A cutting machine for processing a gemstone, the cutting machine comprising:
   a processor to:
   obtain pre-stored marking coordinates associated with a gemstone ID, generated during planning phase of the processing;
   obtain real-time marking coordinates for the gemstone to be processed;
   verify an identity of the gemstone based on a comparison of the pre-stored marking coordinates with the real-time marking coordinates; and
   retrieve information, including cutting parameters, associated with the gemstone ID of the gemstone in response to a valid verification of the identity of the gemstone, for processing the gemstone.

2. The system as claimed in claim 1, wherein the processor is to superimpose the pre-stored marking coordinates with respect to the real-time marking coordinates in a coordinate space.

3. The system as claimed in claim 1, wherein the processor is to verify the identity of the gemstone by superimposing an image indicative of the real-time marking coordinates with an image indicative of the pre-stored marking coordinates to determine a percentage match therebetween, wherein the processor is to relatively rotate the image indicative of the real-time marking coordinates with respect to the image indicative of the pre-stored marking coordinates to compare at predetermined intervals of rotation.

4. The system as claimed in claim 3, wherein the processor is to detect a table line of the gemstone, based on a best-match position of the image indicative of the real-time marking coordinates relative to the image indicative of the pre-stored marking coordinates.

5. The system as claimed in claim 3, wherein the percentage match is compared to a threshold match to determine a best-match for verifying identity of the gemstone.

6. A method for processing a gemstone, the method comprising:
   receiving a marked gemstone, the marked gemstone having markings formed thereon in a planning stage of the processing, wherein the markings are based on marking coordinates associated with the marked gemstone;
   obtaining a set of pre-stored marking coordinates from a database for all planned gemstones;
   generating real-time marking coordinates for the marked gemstone;
   determining best-match pre-stored marking coordinates, based on a comparison of each of the marking coordinates in the set of pre-stored marking coordinates against the real-time marking coordinates; and
   retrieving information, including cutting parameters, associated with a gemstone ID linked to the best-match pre-stored marking coordinates, in response to a valid verification of the identity of the gemstone, for processing the marked gemstone.

7. The method as claimed in claim 6, wherein the determining comprises superimposing the pre-stored marking coordinates with respect to the real-time marking coordinates in a coordinate space.

8. The method as claimed in claim 6, wherein determining comprises superimposing an image indicative of the real-time marking coordinates with an image indicative of the pre-stored marking coordinates to determine a percentage match therebetween, wherein the superimposing comprises relatively rotating the image indicative of the real-time marking coordinates with respect to the image indicative of the pre-stored marking coordinates to compare at predetermined intervals of rotation.

9. The method as claimed in claim 8, further comprising detecting a table line of the gemstone, based on a best-match position of the image indicative of the real-time marking coordinates relative to the image indicative of the pre-stored marking coordinates.

10. A non-transitory computer readable medium comprising instructions executable by a processing resource to:
    receive data corresponding to a marked gemstone, the marked gemstone having markings formed thereon in a planning stage of the processing, wherein the markings are based on marking coordinates associated with the marked gemstone;
    obtain a set of pre-stored marking coordinates from a database for all planned gemstones;
    generate real-time marking coordinates for the marked gemstone;
    determining best-match pre-stored marking coordinates, based on a comparison of each of the marking coordinates in the set of pre-stored marking coordinates against the real-time marking coordinates; and
    retrieve information, including cutting parameters, associated with a gemstone ID linked to the best-match pre-stored marking coordinates, in response to a valid verification of the identity of the gemstone, for processing the marked gemstone.

* * * * *